(12) United States Patent
Jenkins

(10) Patent No.: US 6,381,495 B1
(45) Date of Patent: Apr. 30, 2002

(54) MEDICAL DEVICE FOR USE IN LAPAROSCOPIC SURGERY

(75) Inventor: David A. Jenkins, Flanders, NJ (US)

(73) Assignee: Transneuronix, Inc., Mt. Arlington, NJ (US)

(*) Notice: Subject to any disclaimer, the term of this patent is extended or adjusted under 35 U.S.C. 154(b) by 0 days.

(21) Appl. No.: 09/480,727

(22) Filed: Jan. 10, 2000

Related U.S. Application Data

(63) Continuation-in-part of application No. 09/122,832, filed on Jul. 27, 1998, now Pat. No. 6,041,258, which is a continuation-in-part of application No. PCT/US98/10402, filed on May 21, 1998.

(30) Foreign Application Priority Data

May 29, 1997 (IT) .......................................... Mi97A1246

(51) Int. Cl.[7] .............................. A61N 1/05; A61N 1/18
(52) U.S. Cl. ......................... 607/40; 607/116; 607/115
(58) Field of Search ............................... 607/2, 40, 41, 607/115, 116, 125, 126, 149; 606/223, 222

(56) References Cited

U.S. PATENT DOCUMENTS

| | | | |
|---|---|---|---|
| 2,865,376 A | 12/1958 | Pellier et al. | 606/226 |
| 3,760,812 A | 9/1973 | Timm et al. | 607/116 |
| 4,444,207 A | 4/1984 | Robicsek | 607/132 |
| 4,475,560 A | 10/1984 | Tarjan et al. | 607/128 |
| 4,524,771 A | 6/1985 | McGregor et al. | 606/223 |
| 4,901,722 A | 2/1990 | Noguchi | 606/223 |
| 5,059,207 A | 10/1991 | Shah | 606/223 |
| 5,100,431 A | 3/1992 | Buster et al. | 606/222 |
| 5,300,107 A * | 4/1994 | Stokes et al. | 607/126 |
| 5,423,872 A | 6/1995 | Cigaina | 607/40 |
| 5,423,876 A | 6/1995 | Camps et al. | 607/116 |
| 5,433,728 A | 7/1995 | Kim | 606/223 |
| 5,450,739 A | 9/1995 | Bogart et al. | 72/133 |
| 5,489,294 A | 2/1996 | McVenes et al. | 607/120 |
| 5,683,447 A * | 11/1997 | Bush et al. | 607/126 |
| 5,716,392 A | 2/1998 | Bourgeois et al. | 607/132 |
| 5,755,967 A * | 5/1998 | Doan et al. | 607/126 |
| 5,772,693 A * | 6/1998 | Brownlee | 607/123 |
| 6,006,139 A * | 12/1999 | Kruse et al. | 607/125 |

FOREIGN PATENT DOCUMENTS

| | | | |
|---|---|---|---|
| DE | 44 02 058 | 1/1994 | A61B/5/0408 |
| WO | WO 97/41921 | 11/1997 | A61N/1/32 |

* cited by examiner

Primary Examiner—Carl Layno
(74) Attorney, Agent, or Firm—Fitch, Even, Tabin & Flannery

(57) ABSTRACT

An improved medical implant device for laparoscopic surgery is especially adapted for precise and proper placement of electrode leads relative to tissue to be treated. Once properly placed, the device and the electrode leads can be secured to substantially reduce the risk of displacement during normal movement of tissue. The implant device is adapted for electrostimulation and/or electrical monitoring of endo-abdominal tissue or viscera. The device comprises: 1) an elongated body with immobilizing mechanisms or devices to secure it to the tissue or viscera to be treated, 2) two or more electric poles that are electrically connected to an electric connection terminal for connection to a power source, 3) a mechanism for penetration of the tissue or viscera to be treated, and 4) a quick-release connecting device to separate the penetration device from the elongated body. A unique arrangement of immobilizing mechanisms and poles along the lead body permits easy insertion and placement of the device, and ensures effective electrostimulation and/or electrical monitoring of tissue, viscera, and internal organs of a person (or other mammal's) endo-abdominal cavity.

27 Claims, 3 Drawing Sheets

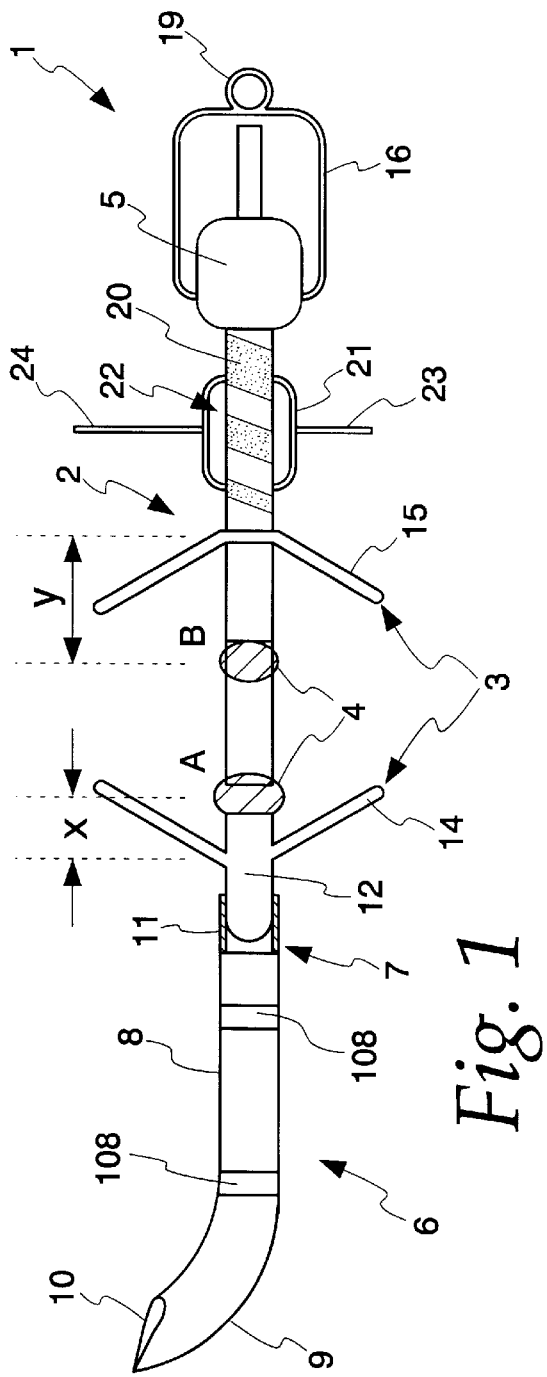

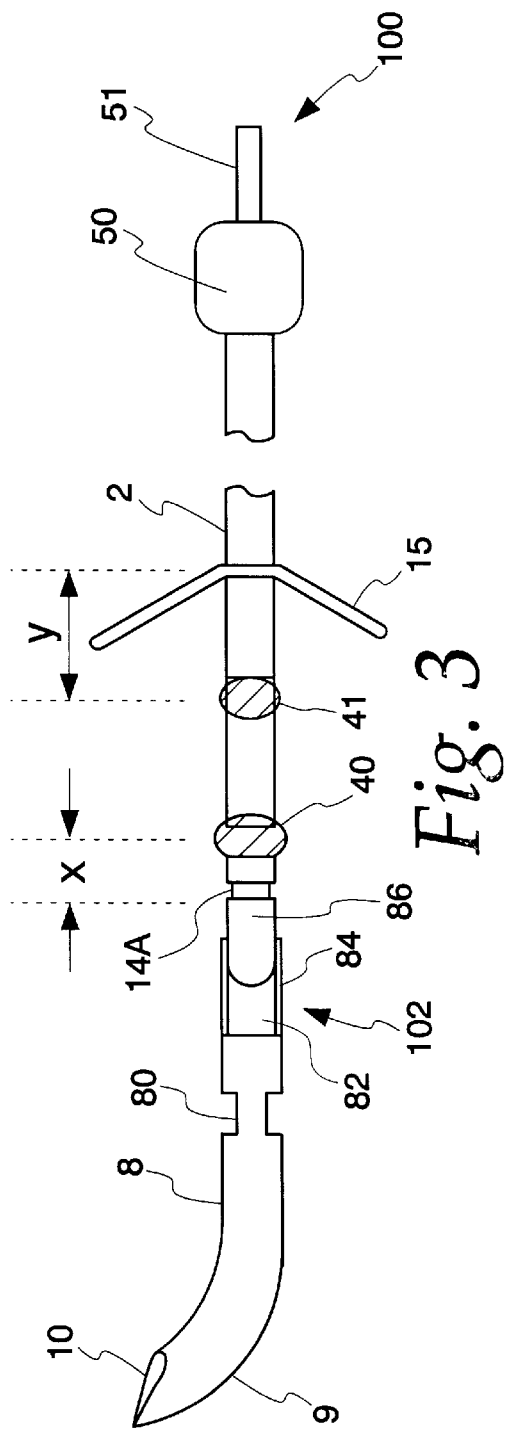
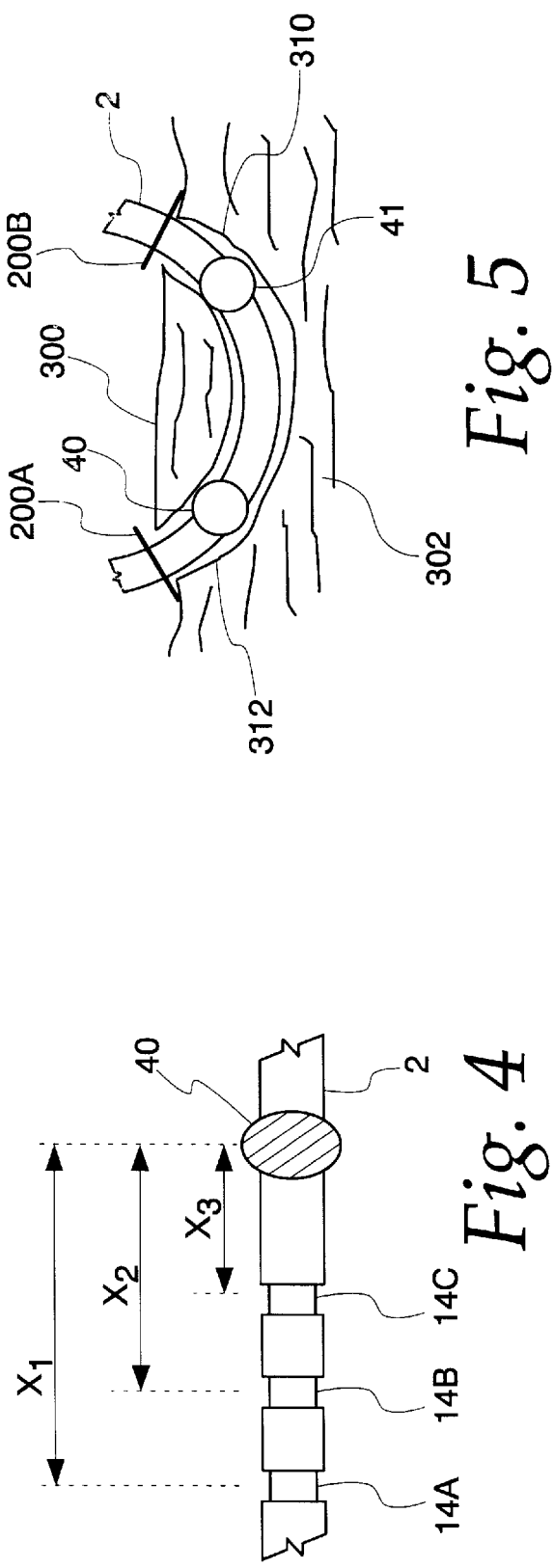

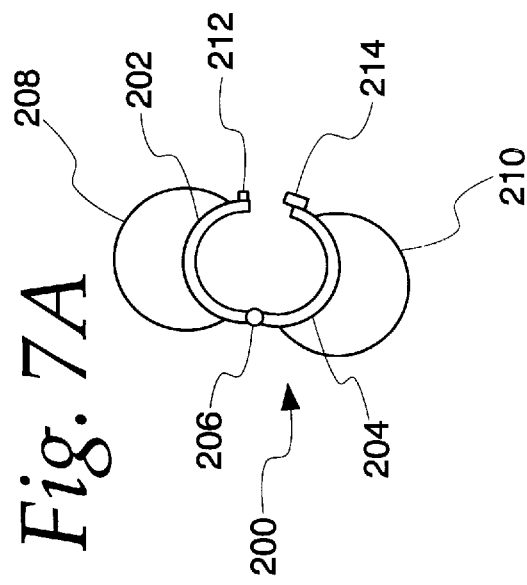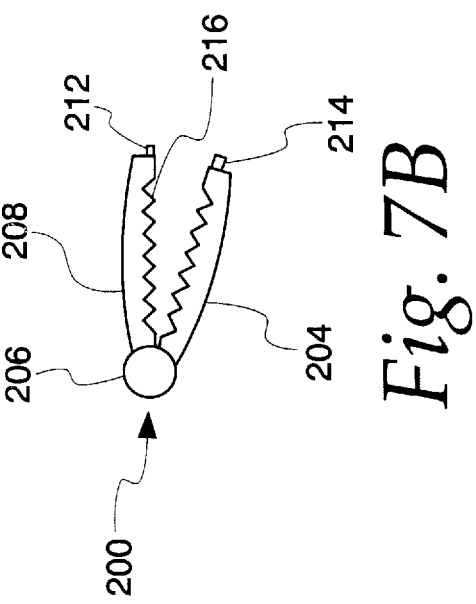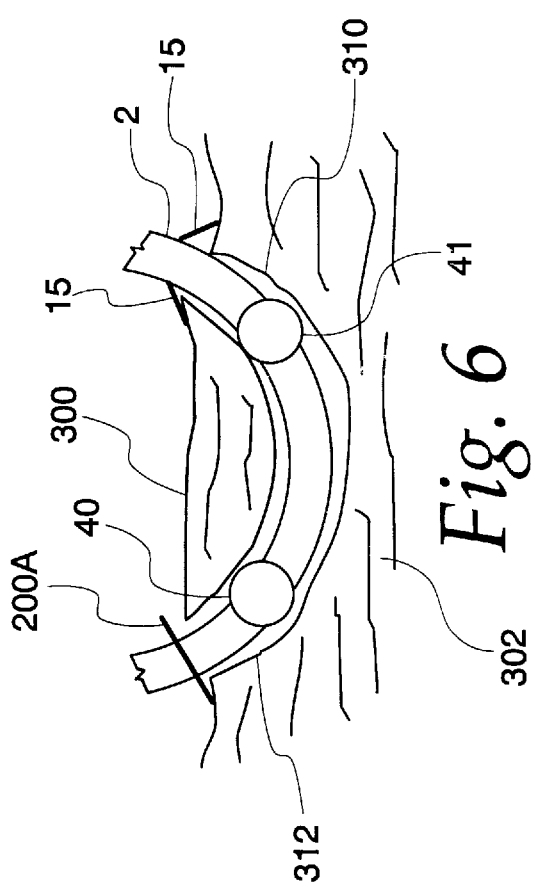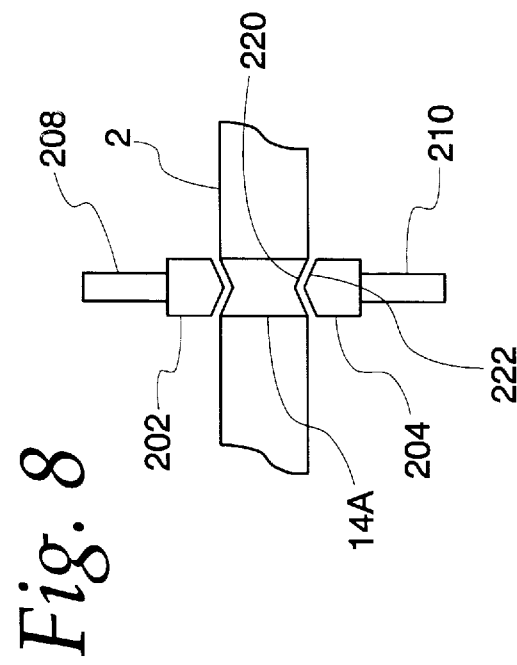

MEDICAL DEVICE FOR USE IN LAPAROSCOPIC SURGERY

RELATED APPLICATIONS

This application is a continuation-in-part of U.S. patent application Ser. No. 09/122,832, now U.S. Pat. No. 6,041, 258 filed Jul. 27, 1998, which is a continuation-in-part of our International Patent Application Serial Number PCT/US98/10402, filed on May 21, 1998, which designated the United States as well as other countries and which claimed priority from Italian Application MI97A001246, filed on May 28, 1997.

FIELD OF THE INVENTION

This invention relates to a medical implant device which is designed and adapted for use in laparoscopic surgery. This medical implant device is especially adapted for electrostimulation and/or electrical monitoring of endo-abdominal tissue or viscera. This medical implant device comprises an elongated body equipped with immobilizing or securing devices to secure it to the tissue or viscera to be treated and two or more electric poles that are electrically connected to an electric connection terminal for connection to a power source, a mechanism to penetrate the tissue or viscera to be treated and quick-release connecting devices to separate the penetration device from the elongated body. The securing devices are especially adapted to properly positioned the implant device within or around tissue to be treated so that good electrical contact with the tissue to be treated can be established and maintained.

BACKGROUND OF THE INVENTION

It is well known that more than 70% of illnesses affecting the digestive tract are of a functional nature. Today such illnesses are treated predominantly using pharmacological means. Since drugs generally have side effects, particularly when the drugs cure the symptom and not the underlying problem or dysfunction, they must often be administered temporally. Indeed, if the side effects are sufficiently serious, the drug may have to be discontinued before full benefit to the patient is realized; in many cases the underlying illness remains.

The important role played by electrophysiology in controlling gastrointestinal activity has become increasingly apparent in recent years. Thus, the possibility exits of correcting dysfunction by means of electrostimulation applied at specific frequencies, sites, and modalities and with regard to the self-regulating electromotor physiology of the gastrointestinal organs or tract. It has recently been shown, for example, that changes occur in the motility and electromotor conduct of the gastric tract in eating disorders (e.g., obesity, thinness, bulimia, anorexia). Disturbances in electromotor activity in diabetic gastroparesis, reflux in the upper digestive tract, and numerous other gastroenterological functional pathologies have also been observed.

Stimulation of the intrinsic nervous system of the stomach is likely to have two major consequences or effects: (1) the correction and direct control of the electromotor activity of the intestines and (2) the stimulation of increased incretion of specific substances (i.e., gastroenteric neuromediators) produced by the intrinsic nervous system itself through the myenteric plexus. Curing of functional illnesses involving the digestive system and, more broadly, involving disorders in any way connected to, or associated with, the digestive system is, therefore, closely linked to the progress of research in the field of electrophysiology.

An indispensable condition for modifying the electrical activity of the digestive system's intestinal tract and related neurohormonal incretions is the use of an implant system to generate electrical impulses (electrical stimuli) and means (e.g., electrocatheters) to connect them to the viscera and/or intestines to be stimulated. These treatment methods involve an "invasive" surgical technique to implant the electrocatheter in the abdomen. This may involve open or, preferably, micro-invasive surgery (i.e., video-laparoscopic surgery). Current electrocatheters to stimulate electrically and/or monitor endo-abdominal viscera may have metal microbarbs which are angled in such a way as to permit application of the end of the catheter and to prevent it subsequently from being dislodged. However, metal microbarbs can damage surrounding tissue especially when exposed to the vigorous action of the digestive tissue and/or organs. Among the undesirable consequences of such damage is erosion of the electrode into the lumen of the gastrointestinal tract. This would result in contamination of the abdominal cavity and the electrode The subsequent infection would, at a minimum, require removal of the catheter and involve an additional operation.

During laparoscopic procedures, after administering a general anesthetic, the patient's abdomen is inflated with $CO_2$ or another inert inflammable gas, thereby transforming the abdominal cavity from a virtual to a real cavity. Rigid tubes with air-tight valve mechanisms ("trocars") are then inserted into the gas-filled abdominal cavity so that a video camera and other surgical instruments can be introduced into the abdomen. The operation then proceeds by viewing the video images transmitted by the camera. Multiple trocars are required. Generally, the first trocar provides access to the abdomen by the video camera in order to monitor the surgical procedure. A clamp is normally inserted in the second trocar to move or retain the hepatic edge that normally covers the lesser curve of the stomach or other viscera depending on the type of operation to be performed. A third trocar provides access for a maneuvering clamp or laparoscopic forceps. The fourth trocar is used for the introduction of instruments as well as the electrocatheter to be implanted in the stomach wall of the patient. The structure of the electrocatheter plays an important part in facilitating the specific operation for whichever of the patient's organs and/or viscera the surgeon aims to stimulate.

Each of the trocars used, of course, requires a separate tract through the skin and abdominal wall. To keep the abdomen inflated, valves are used with the trocars to provide a gas-tight seal. Introduction of a medical device, such as an electrocatheter or implantable electrode, into the abdomen generally requires the use of laparoscopic forceps to grasp the device. Such devices, which are generally inherently fragile in nature, could be damaged if grasped too firmly by the forceps. Thus, for example in the case of an electrocatheter having electrode leads, the interior conductor wires could be broken, rendering the device dysfunctionally or completely useless.

It is also desirable to place the electrocatheter adjacent to the tissue or organ of interest and "lock" it in place so that the target tissue or organ can then be electrostimulated and/or electrically monitored. As noted above, metal microbarbs have been used to lock the device in place. Such metal microbarbs can damage or tear surrounding tissue— especially when the implant device is subjected to the vigorous action or peristaltic movement of the digestive organs. More recently, flexible microbarbs have been used for such implant device. Although such flexible microbarbs are less likely to damage the surrounding tissue, so-equipped electrocatheters can be difficult to precisely place and position relative to the tissue to be treated. In some cases, one of the electrodes is actually outside the penetration tunnel and, thus, not in direct contact with the tissue to be treated. Indeed, both electrodes can be outside the penetration tunnel. Of course, the lack of contact of at least one electrode with the tissue will result in inferior electrostimulation and/or monitoring of the tissue to be treated. Moreover, since, for example, stomach muscle is somewhat flaccid, it is often difficult to push or pull the implant device, especially under conditions of laparoscopic surgery, so that both electrodes are in good electrical contact with the target tissue. Even in cases where the electrodes are initially positioned properly (i.e., both electrodes within the penetration tunnel and in contract with the tissue walls forming the penetration tunnel), movement of the elongated body within the penetration tunnel can sometimes allow at least one of the electrodes to move outside the penetration tunnel and lose contact with the tissue. Of course, with tissue or organs undergoing vigorously movement (e.g., the stomach during digestion), there is an increased likelihood that one of the electrodes may migrate to a position outside the penetration tunnel.

It would be desirable, therefore, to provide an improved implant device which can be easily and precisely positioned for attachment to the target tissue or organ and which can be securely locked in place. It would also be desirable to provide an improved implant device with an immobilizing mechanism which allows the electrode leads to be easily placed in good electrical contact with target tissue or organ. It would also be desirable to provide an improved implant device with an immobilizing mechanism which, once placed so that the electrode leads are in good electrical contact with target tissue or organ, will resist movement or displacement of the electrode leads such that good electrical contact is not significantly impaired. Such an immobilizing mechanisms would be especially desirable in cases where the tissue is undergoing repeated and/or vigorous movement (e.g., stomach muscle during digestion). It would also be desirable to provide an improved implant device which will resist displacement by the vigorous movement of internal organs or viscera within the abdominal or other body cavities over prolonged or extended periods of time. The present invention provides such implant devices. Although the implant devices of the present invention are especially adapted for implantation within the abdominal cavity, they can also be used throughout the body. The present implant devices allow precise placement of the electrode leads relative to the tissue to be treated and resist displacement from tissue or organs which undergo repeated and/or vigorous movement. The present implant device would be especially useful, for example, within the abdominal cavity or the thoracic cavity.

SUMMARY OF THE INVENTION

This invention relates to a medical implant device which is designed and adapted for use in laparoscopic surgery. This medical implant device is especially adapted for precise and proper placement of the electrode leads relative to the tissue to be treated. Additionally, the medical implant device, once properly placed, can be secured so as to substantially reduce the risk of displacement of the device, and especially the electrode leads, during normal movement of the tissue. This medical implant device is especially adapted for electrostimulation and/or electrical monitoring of endo-abdominal tissue or viscera. Generally, the implant devices of this invention have an elongated body equipped with immobilizing mechanisms or devices to secure it to the tissue or viscera to be treated, two or more electric poles that are electrically connected to an electric connection terminal for connection to a power source, a mechanism for penetration of the tissue or viscera to be treated, and a quick-release connecting device to separate the penetration device from the elongated body. The improved medical implant device of this invention is obtained by precisely controlling the relative positioning of the electrode leads and the immobilizing mechanisms along the elongated body. This implant device can be easily inserted and properly placed or anchored in the viscera to be stimulated. This improved implant device includes electric poles and immobilizing components properly disposed with respect to each other to ensure effective electrostimulation and/or electrical monitoring of the tissue or viscera of the mammalian body (especially the human body), especially tissue and internal organs the endo-abdominal cavity. Examples of such tissue and internal organs include, but are not limited to, the stomach, small intestine, large intestine, urinary bladder, gall bladder, muscles of the abdominal cavity, and tissue, muscles, and/or organs of the thoracic cavity (including, but not limited to, the cervical, thoracic, and abdominal portions of the esophagus and the pharyngeal musculature in the neck), and the like.

It is one object of the present invention to provide an improved medical device to be used in laparoscopic surgery which can be positioned easily and precisely such that the electrodes are in good electrical contact with the tissue to be treated. A further object of the invention is to provide an implant device for electrostimulation or electrical monitoring of tissue to be treated within a body cavity, said implant device comprising (1) an elongated body having a distal end and a proximal end, (2) a penetration mechanism at the distal end to penetrate the tissue to be treated, (3) a quick release connecting mechanism adjacent to the penetration mechanism, (4) a first immobilizing mechanism and a second immobilizing mechanism adjacent and proximal to the quick release connecting mechanism to secure the implant device to the tissue to be treated wherein the first and second immobilizing mechanisms are spaced apart along the elongated body a distance sufficient to span the tissue such that the first immobilizing mechanism is located between the quick release connecting mechanism and the second immobilizing mechanism, (5) a first and second electric poles located between the first and second immobilizing mechanisms, such that the first electric pole is adjacent to the first immobilizing mechanism and the second electric pole is adjacent to the second immobilizing mechanism, and (6) an electrical connection terminal at the proximal end for connection to a power source; wherein the first and second electric poles are electrically connected to the electrical connection terminal; wherein the quick release connecting mechanism is effective to separate the penetration device from the elongated body once the implant device is properly positioned in the body cavity; and wherein the first immobilizing mechanism is located at a distance of about 5 mm or greater from the first electric pole and the second immobilizing mechanism is located at a distance of about 5 mm or greater from the second electric pole. Preferably, the distance from the first immobilizing mechanism to the first electric pole is about 5 to about 20 mm and the distance from the second immobilizing mechanism to the second electric pole is 5 to about 20 mm.

A still further object of the invention is to provide an implant device for electrostimulation or electrical monitoring of tissue to be treated within the endo-abdominal cavity, said implant device comprising (1) an elongated body having a distal end and a proximal end, (2) a penetration mechanism at the distal end to penetrate the tissue to be treated and to form a penetration tunnel though the tissue, wherein the penetration tunnel has a distal terminus and a proximal terminus and a length as measured from the distal terminus to the proximal terminus through the penetration tunnel, (3) a quick release connecting mechanism adjacent to the penetration mechanism, (4) a first immobilizing mechanism and a second immobilizing mechanism, wherein the second immobilizing mechanism is attached to, and integral, with the elongated body and is proximal to the quick release connecting mechanism such that second immobilizing unit will engage the proximal terminus of the penetration tunnel and wherein the first immobilizing mechanism is adapted to be affixed to the elongated body as its exits the distal terminus of the penetration tunnel to secure the implant device to the tissue to be treated, (5) a first and second electric poles located between the first and second immobilizing mechanisms, such that the first electric pole is adjacent to the first immobilizing mechanism and the second electric pole is adjacent to the second immobilizing mechanism and wherein the first and second electric poles are in good electrical contact with the tissue forming the penetration tunnel, and (6) an electrical connection terminal at the proximal end for connection to a power source; wherein the first and second electric poles are electrically connected to the electrical connection terminal; wherein the quick release connecting mechanism is effective to separate the penetration device from the elongated body once the implant device is properly positioned in the endo-abdominal cavity; wherein the first immobilizing mechanism is located at a distance of about 5 mm or greater from the first electric pole and the second immobilizing mechanism is located at a distance of about 5 mm or greater than from the second electric pole, and wherein the first and second immobilizing mechanism are spaced apart a distance approximately equal to, or less than, the length of the penetration tunnel. Preferably the distance from the first immobilizing unit to the first electric pole is about 5 to about 20 mm and the distance from the second immobilizing mechanism to the second electric pole is about 5 to about 15 mm.

A still further object of the invention is to provide an implant device for electrostimulation or electrical monitoring of tissue to be treated within the endo-abdominal cavity, said implant device comprising (1) an elongated body having a distal end and a proximal end, (2) a penetration mechanism at the distal end to penetrate the tissue to be treated and to form a penetration tunnel though the tissue, wherein the penetration tunnel has a distal terminus and a proximal terminus and a length as measured through the penetration tunnel from the proximal terminus to the distal terminus, (3) a quick release connecting mechanism adjacent to the penetration mechanism, (4) a first immobilizing mechanism which can be attached to the elongated body to secure it in place within the penetration tunnel once the elongated body is properly positioned relative to the tissue to be treated and a second immobilizing mechanism which can be attached to the elongated body to secure it in place within the penetration tunnel either before or after the elongated body is properly positioned relative to the tissue to be treated, wherein the first immobilizing mechanism is adapted to be attached to the elongated body at the distal terminus of the penetration tunnel and the second immobilizing mechanism is adapted to be attached to the elongated body at the proximal terminus of the penetration tunnel, (5) a first electric pole and a second electric pole spaced apart along the elongated body to be contained within the penetration tunnel and to be in good electrical contact with the tissue forming the penetration tunnel, and (6) an electrical connection terminal at the proximal end for connection to a power source; wherein the first and second electric poles are electrically connected to the electrical connection terminal; wherein the quick release connecting mechanism is effective to separate the penetration device from the elongated body once the implant device is properly positioned in the endo-abdominal cavity; wherein, when the first and second electric poles are properly situated within the penetration tunnel, the first immobilizing mechanism is located at a distance of about 5 mm or greater from the first electric pole and the second immobilizing mechanism is located at a distance of about 5 mm or greater from the second electric pole, and wherein the first and second immobilizing mechanism are spaced apart a distance approximately equal to, or less than, the length of the penetration tunnel. Preferably the distance from the first immobilizing unit to the first electric pole is about 5 to about 20 mm and the distance from the second immobilizing mechanism to the second electric pole is about 5 to about 15 mm.

Another object of the present invention is to provide a laparoscopic surgical method for attaching an implant device to tissue to be treated, said method comprising (a) inserting an implant device though a trocar into a body cavity containing the tissue to be treated, wherein the implant device has a penetration mechanism and a first and second electric poles, (b) forming a penetration tunnel within the tissue to be treated using the penetration mechanism, wherein the penetration tunnel has a distal terminus and a proximal terminus and a length as measured through the penetration tunnel from the proximal terminus to the distal terminus, (c) positioning the first and second electric poles within the penetration tunnel to provide good electrical contact with the tissue to be treated, and (d) immobilizing the implant device within the penetration tunnel so as to maintain good electrical contact between the first electric pole and the tissue to be treated and between the second electric pole and the tissue to be treated during a treatment regime; wherein the implant device comprises (1) an elongated body having a distal end and a proximal end, (2) penetration mechanism which is located at the distal end to penetrate and to form the penetration tunnel in the tissue to be treated, (3) a quick release connecting mechanism adjacent to the penetration mechanism, (4) a first immobilizing mechanism and a second immobilizing mechanism adjacent and proximal to the quick release connecting mechanism to immobilize the implant device to the tissue to be treated wherein the first and second immobilizing mechanisms are spaced apart along the elongated body a distance sufficient to span the tissue such that the first immobilizing mechanism is located between the quick release connecting mechanism and the second immobilizing mechanism, (5) first and second electric poles which are located between the first and second immobilizing mechanisms, such that the first electric pole is adjacent to the first immobilizing mechanism and the second electric pole is adjacent to the second immobilizing mechanism, and (6) an electrical connection terminal at the proximal end for connection to a power source; wherein the first and second electric poles are electrically connected to the electrical connection terminal; wherein the quick release connecting mechanism is effective to separate the penetration device from the elongated body once the first and second electric poles are properly positioned within the penetration tunnel; and wherein, when the first and second electric poles are properly situated within the penetration tunnel, the first immobilizing mechanism is located at a distance of about 5 mm or greater from the first electric pole and the second immobilizing mechanism is located at a distance of about 5 mm or greater from the second electric pole, and wherein the first and second immobilizing mechanism are spaced apart a distance approximately equal to, or less than, the length of the penetration tunnel.

Yet another object of the present invention is to provide a method for electrostimulation of gastrointestinal tissue, said method comprising (a) inserting an implant device though a trocar into the endo-adominal cavity, wherein the implant device has a first and second electric poles and an electrical connection terminal for connection to an electrical pulse generator, (b) positioning the first and second electric poles within an area of the gastrointestinal track to provide good electrical stimulation with the Auerbach plexus and the Meissner plexus, (c) immobilizing the implant device so as to maintain good electrical stimulation of the Auerbach plexus and the Meissner plexus during a treatment regime, (d) attaching the electrical pulse generator to the electrical connection terminal of the implant device, and (e) delivering electrical impulses to the implant device and thereby electrically stimulating the Auerbach plexus and the Meissner plexus.

These and other features and advantages of the present invention will become apparent to those skilled in the art upon a reading of the following detailed description when taken in conjunction with the drawings wherein there is shown and described preferred embodiments of the invention.

BRIEF DESCRIPTION OF THE DRAWINGS

FIG. 1 is a schematic side view of one embodiment of the implant device according to this invention wherein the first and second immobilizing mechanisms are sets of flexible tines.

FIG. 2 is a schematic side view of another embodiment of the implant device according to this invention wherein the first and second immobilizing mechanisms are sets of flexible tines and wherein the penetration device has been removed via the quick release mechanism.

FIG. 3 is a schematic side view of another embodiment of the implant device according to this invention wherein the first (or distal) immobilizing mechanism is a clamp or other locking device which is affixed to the clamping position 14A on the distal elongated body once the implant device is properly positioned within the penetration tunnel and wherein the second (or proximal) immobilizing mechanism is a set of flexible tines to engage the proximal terminus of the penetration tunnel.

FIG. 4 illustrates a portion of an electrocatheter having three clamping positions 14A, 14B, and 14C for accepting a clamping mechanism once the implant device is properly positioned within the penetration tunnel.

FIG. 5 illustrates one embodiment of the electrocatheter placed within stomach muscle for electrostimulation of the stomach. The immobilizing mechanisms are clamps which are attached to the elongated body at both the proximal and distal ends of the penetration tunnel once the electrocatheter has been properly positioned within the penetration tunnel.

FIG. 6 illustrates another embodiment of the electrocatheter placed within stomach muscle for electrostimulation of the stomach. The immobilizing mechanisms are, at the proximal end, a set of angled tines and, at the distal end, a clamp which is attached to the elongated body at the distal end of the penetration tunnel once the electrocatheter has been properly positioned within the penetration tunnel.

FIG. 7 illustrates clamps which can be used to lock the electrocatheter of this invention in place once the electrocatheter has been properly positioned.

FIG. 8 illustrates a clamping position along the elongated body and a clamp having matching clamping surfaces.

DETAILED DESCRIPTION OF THE PREFERRED EMBODIMENTS

The present invention provides an implant device specifically for electrostimulation and/or electrical monitoring of the endo-abdominal visceral tract and which can easily and precisely positioned within the tissue to be treated in order to insure good electrical contact between the electric poles of the implant device and the tissue to be treated. The implant device has an elongated body equipped with immobilizing mechanisms or devices to secure it to the gastrointestinal wall and two or more electric poles that are electrically connected to an electrical connection terminal for connection to a power source, characterized by the fact that it includes a mechanism to penetrate the gastrointestinal wall and a quick release connecting mechanism to separate said penetration device from the elongated body. Various embodiments of the present invention are illustrated in FIGS. 1–3. FIGS. 4–6 illustrate the immobilizing units and their relationship to the electric poles and the penetration tunnel formed in the tissue to be treated; other elements of the implant device are not shown in these figures. The implant device specifically for electrostimulation and/or electrical monitoring of the endo-abdominal viscera is identified overall by reference number 1, and includes an elongated body 2 of the electrocatheter equipped with securing mechanisms 3 (consisting of tines 14 and 15 in FIGS. 1 and 2; and tines 15 and position 14A for attachment of a clamp (not shown) in FIG. 3) to lock the distal end of the electrocatheter in place and to secure it to the visceral wall (not shown), and two or more electric poles 4A (distal) and 4B (proximal) which are electrically connected to an electrical connection terminal pin 5 that is capable of connecting the electrocatheter to a power source (not shown). The power source may be, for example, an electric pulsator with an operating frequency of a preset number of pulses per minute. Throughout this discussion, the distal side or end of the implant or elements is considered to be in the direction of the penetration mechanism 6 and the proximal side or end is considered to be in the direction of the electrical connection terminal pin 5 in FIGS. 1 and 2 and proximal end 100 in FIG. 3; more generally the distal end or direction is towards the left and the proximal end or direction is towards the right in the figures.

More specifically, the implant device includes penetration mechanism 6 capable of penetrating the gastrointestinal wall and forming a penetration tunnel in the tissue to be treated and mechanism 7 for connection and quick-release of penetration mechanism 6 to the elongated body 2 of the electrocatheter. In particular, penetration mechanism 6 includes a solid tunneling device or stylet 8 with a smooth, noncutting curved section 9 on the end of which is cutting part 10. Located opposite end 10 is cavity 11 through which the attachment to the elongated body 2 is made. The connection and quick-release mechanism 7 includes a connecting element 12, one end of which is connected to the end of elongated body 2, and the other end of which is connected to the inside of cavity 11 on stylet 8.

The outer insulating cover on elongated body 2 and connecting element 12 are preferably formed from silicone (preferably medical grade) or other biocompatible material having similar characteristics. The length of the connecting element 12 is adjusted to permit angling and flexibility without harming the electrical component located within the elongated body. In addition, the connecting element 12 preferably is radiopaque. Advantageously, during video-laparoscopic surgery, in order to separate the stylet 8 from the elongated body 2 of the electrocatheter, it is sufficient to cut it with scissors as shown in FIG. 2 in order to be able to remove the stylet from the abdominal cavity, as will be better explained below.

Furthermore, as can easily be seen from FIGS. 1 and 2, connecting element 12 also has securing parts 3, which in the embodiment shown in FIGS. 1 and 2 include, in particular a first set of projections, wings, or tines 14 which are spread apart and are elastically pliable. Preferably, the securing parts 3 and tines 14 are also made of silicone, but are not radiopaque. Opposite the plurality of first tines 14, the elongated body 2 is equipped with a plurality of second tines 15, which are spread apart in the opposite directions from the first tines and are designed to define the deepest point of penetration of the elongated body into the visceral wall. Generally, both the first and second tines are each at least two in number; preferably each set of tines are three to five in number. Preferably, the first tines 14 and the second tines 15 have a diameter of about 1 mm and a length of about 3 mm. As those skilled in the art will realize, both the first and second set of tines may be of different numbers, sizes, and shapes so long as they serve their intended purpose of "locking" the implant to the tissue or viscera to be stimulated and/or monitored. The tines are flexible and are preferably formed from silicone (preferably medical grade) or other bio-compatible materials in order to minimize damage or stress to the tissue as the implant device is positioned and, after completion of treatment, removed.

The relative distance of tines 14 to electric pole 4A (denoted by "x" in FIGS. 1–3) and of tine 15 to electric pole 14B (denoted by "y" in FIGS. 1–3) are critical parameters in the present invention. More specifically, the distance x is greater than about 5 mm and preferably about 5 to about 20 mm for the distal pair of tine 14 and electric pole 4A and the distance y is greater than about 5 mm and preferably about 5 to about 15 mm for the proximal pair of tine 15 and electric pole 4B. By carefully controlling these two parameters, the implant can be easily and precisely positioned within the penetration tunnel so that the electric poles 4A and 4B are in good electrical contact with the tissue to be treated. The distances of the electric poles from either end of the penetration tunnel formed by the penetration device 6 are of sufficient lengths so as significantly reduce the risk that either electric pole 4A or 4B can migrate to a position outside of the penetration tunnel and lose the desired electrical contact between the electrical poles and the tissue to be treated.

In operation, the second tines 15 do not penetrate the thickness of the gastrointestinal wall or other tissue to be stimulated. Rather, they work with the first pair to prevent the electrocatheter from being dislodged after insertion (see also FIG. 6). In effect, the two sets of tines 14 and 15 allow the electrocatheter to be "locked" in place relative to the tissue to be stimulated without the need for any suturing to anchor the electrocatheter. The distance between the first and second pair of tines may be varied as needed (so long as the distances x and y remain within the desired ranges) and will depend upon the desired distance between the two electric poles 4A and 4B. Of course, the desired distance between the two poles will be related to the thickness of the tissue intended to be stimulated. The distance between the electric poles can also vary depending upon whether the electrical simulator is used only for stimulation or for electrical monitoring and/or whether an electrocatheter with more than two electric poles is to be used. Preferably, the distance between the first and second immobilizing mechanisms is approximately equal to, or less than, the length of the penetration tunnel. Preferably, the linear part of stylet 8 has a length that is at least equal to the distance between the first and second sets of tines 14 and 15. Additionally, the stylet 8 may have markings 108 (see FIGS. 1 and 2) or other identifying labels which aid the surgeon in assessing the correct penetration tunnel length and, therefore, the proper placement of the implant device. Such markings 108 could, for example, imprinted, etched, colored, or scribed on the surface of the stylet to indicate the appropriate distance that would insure that the electrode leads are properly positioned within the penetration tunnel (i.e., fully contained within the penetration tunnel).

The implant device (as shown in FIGS. 1 and 2) may also include a cover or cap 16 that consists, for instance, of a removable and insulating sheath which has, in addition, sealing element 18. The sheath includes a small covering, also of silicone, which guarantees both the impermeability of connecting terminal 5 for the entire time it is in the abdomen during insertion, and during its recovery for electrical connection. For this reason the sheath includes the sealing element consisting of binding 18 which keeps it watertight, prevents any contact between the biological fluids and electric terminal 5, and prevents the sheath from breaking off by force of the traction to which it is subjected when the electrical connecting terminal is extracted from the abdomen. The sheath is, moreover, equipped with a mechanism to recover the electrocatheter after implanting, which consists of ring 19 which can be attached to thread 30 of a predetermined length. The unattached end of thread 30 remains outside the abdominal cavity and thereby permits recovery of the electric terminal end of the electrocatheter.

If desired, the elongated body may have a series of graphic representations 20, each one of which is different from the other, which can be used to indicate the orientation and location of the electrocatheter during the implant procedure. For example, the graphic representations could consist of black (or other colored) zebra stripes that increase in size as they moves toward electric terminal 5. Of course, other graphic representations could be used so long as they allow the orientation and location of the electrocatheter to be determined visually (through the video camera) during the implantation procedure.

In addition, the elongated body shown in FIGS. 1 and 2 has a sliding cylindrical cursor 21 equipped with a seat 22 which permits it to be stopped at a desired position on the elongated body. The cursor has a discoidal extension 23 with one or more small holes 24 through which thread 25 may be inserted, which permits the electrocatheter, if desired, to be attached to a membrane outside the abdominal cavity. After the electrocatheter is anchored to the viscera (i.e., the tissue to be stimulated and/or monitored), the surgeon can move the small cylinder to the desired position on the electrocatheter and attach it to the outside of the abdominal cavity so as to reduce to a minimum the excessive length of the electrocatheter inside the abdomen itself.

In operation, once the patient has been given a general anesthesia and the appropriate trocars have been inserted, it is possible to maneuver from outside all the instruments that are used by means of a monitor that transmits the images from the video camera. At this point, the surgeon should see to it that sheath 16 is tightly secured by binding 18 to the electrical terminal 5. Then the surgeon proceeds to connect thread 30 to ring 19 attached to sheath 16. After the electrocatheter is placed in the abdominal cavity, the surgeon keeps thread 30, which is anchored to the ring 19 and must be of sufficient length, outside the abdomen. By means of the live images from the camera it is easy to identify the back end of the electrocatheter thanks to the zebra stripes 20, and thus, stylet 8 which is secured by a needle holder or clamp is introduced into the thickness of the small gastric curve, taking care not to enter the gastric cavity. For this purpose, a gastroscopy may be performed during the tunneling operation.

When stylet 8 has completed its journey, it is gently pushed so as to cause the first pair of tines 14 (or clamping position 14A) to exit the tunnel created by the stylet. The second pair of tines 15 stops outside the tunnel created by the stylet. In this position, the tissue to be stimulated is located between the two pairs of tines 14 and 15. Moreover, the electrocatheter is effectively "locked" in place by the two pairs of tines 14 and 15. Positioned between the two sets of tines, and therefore inside the transmuscular tunnel, are two or more electrical poles 4A and 4B to stimulate the gastric wall.

Once the electrocatheter is properly position, the stylet 8 is then again secured with forceps, and quick release connecting element 12 is cut easily and simply with endoscopic scissors as shown in FIG. 2. The stylet is then removed from the abdominal cavity of the patient. Using thread 30 attached to ring 19 on sheath 16, the electric terminal may be extracted from the abdomen for connecting to an appropriate power source or an electric simulator such as, for example, a pacemaker or electric recorder.

Once the electric terminal is outside the abdomen, small loop 18 is removed and sheath 16 is removed from electric terminal 5 in order to expose the electric terminal. This operation can be performed in a dry arena. Electric terminal 5 is then connected to a pacemaker or a recorder, and the proper functioning of the system and the integrity of the electrocatheter are checked using the appropriate instrument. After gently pulling the electrocatheter toward the outside so as to reduce to a minimum length its presence in the abdomen, cursor 21 is slid towards the abdominal wall and is then secured to the electrocatheter using, for example, a nylon thread or suture. If desired, the electrocatheter can be anchored via extension 23, by means of thread 25, to the abdominal wall, preferably to the muscular fascia, by a nylon suture. In this manner, the electrocatheter is secured in two positions: (1) around the tissue to be stimulated by tines 14 and 15 and (2) to the abdominal wall via extension 23.

A simplified embodiment of the present electrocatheter is shown in FIG. 3. This embodiment also illustrates the use of an alternative locking mechanism wherein the distal set of tines is replace with clamping position 14A designed to accept a clamp (examples of suitable clamps are shown in FIG. 7). In this embodiment, the stylet 8 is attached to the elongated body 2 at distal end 102. The stylet 8 in this embodiment is attached to the elongated body 2 using a flexible tube 84 (preferably medical-grade silicone similar to the insulating cover of the elongated body 2) that fits over the end 86 of elongated body 2 and the hub 82 of stylet 8. The connection may be strengthen, if desired, using medical-grade adhesive and/or a thin wire or thread (or wires or threads) joining the stylet 8 and the elongated body 2. Of course, if such a wire or thread is used to strengthen the connection, it should be non-conducting or electrically isolated from the electrical circuit used for stimulation. The elongated body has only one set of tines or wings 15 and appropriate poles 40 and 41 located distal to tines 15. The distance y (i.e., the distance between electric pole 41 and tines 15) is greater than about 5 mm and preferably about 5 to about 15 mm. The distal set of tines shown in FIGS. 1 and 2 is replaced in the embodiment shown in FIG. 3 with a position 14A placed on the elongated body 2 distal to electric pole 40. Position 14A is designed to receive a clamp or other locking device once the implant is properly positioned within the penetration tunnel formed in the tissue to be treated. The distance between position 14A and electric pole 40 is about greater than about 5 mm and preferably 5 to about 20 mm. Again, these relative distances are designed to ensure that the electric poles 40 and 41 are properly placed within the penetration tunnel to achieve good electrical contact with the tissue to be treated.

The elongated body 2 terminates in electrical terminal 5 having electrical poles 50 and 51 at proximal end 100. In operation, the electrocatheter is placed and positioned in essentially the same manner as described above for the embodiment shown in FIGS. 1 and 2 except that (1) the electrical terminal 5 preferably remains outside the body cavity and (2) once properly positioned within the penetration tunnel, a clamp is placed at position 14A to lock the electrocatheter in place. In some instances, it may be desirable to separate the penetration device 6 only after the clamp has been attached at position 14A thereby allowing the surgeon to more easily grasp and hold the implant (especially at flattened notch 80) while the clamp is being placed at position 14A. Once the electrocatheter has been correctly positioned within the body cavity, the electrical terminal 5 can be attached to the appropriate power source. Thus, the simplified electrocatheter shown in FIG. 3 does not require the movable cursor 21 or the sheath 16 to protect the electrical terminal 5 (although they can be used if desired) since the electrical terminal 5 remains outside the body cavity during the implantation procedure. Preferably the stylet 8 has one or more flattened portions 80 to help the surgeon grasp, manipulate, and guide the implant device to the proper position using forceps or other surgical instruments. Although not shown in FIG. 3, the proximal set of tines 15 could be replaced with a clamping position similar to 14A.

In operation, the electrocatheter shown in FIG. 3 is placed using essentially the same surgical procedure as described above except for placement of the clamp at position 14A. Once in place, the two poles 50 and 51 of electrical terminal 5 are attached to a power source. One pole 50 of the electrical terminal 5 is electrically connected to one pole 41 and the other pole 51 of the electrical terminal 5 is electrically connected to the other pole 40 through the elongated body. The electrical circuit is completed via the tissue to be stimulated and/or monitored. Thus, as those skilled in the art will understand, the overall electrical circuit within the implant device runs from one pole 51 of the electrical terminal 5 along a first electrical path through the elongated body 2 to electric pole 40, through the tissue to be stimulated to the other electric pole 41, and then from the other electric pole 41 through a second and separate electric path through the elongated body 2 to the other pole 50 in the electrical terminal 5. As those skilled in the art will also realize, the materials of construction and the methods of making the electrical circuit for the implant devices of this invention, including the poles 40, 41, 50, and 51 as well as the internal electrical connections, are well known in the art.

Of course, more than one position 14A can be located on the elongated body. For example, three such positions 14A, 14B, and 14C are shown in FIG. 4 at the distal end of the electrocatheter. In this case, position 14A is located a distance $x_1$ from the electric pole 40; 14B is a distance $x_2$ from the electric pole; and 14C is a distance $x_3$ from the electric pole. Since the position of the distal clamp preferably should be about 5 to about 20 mm from the electric pole, $x_1$ would normally be about 20 mm from the electric pole, $x_2$ about 12 to 13 mm, and $x_3$ about 20 mm. Using multiple positioning sites, the surgeon could select the best position for the particular implant location and then lock the implant in place. The proximal immobilizing unit could employ the tines shown in FIGS. 1 and 2 or the clamping mechanism as shown in FIGS. 3 or 4. As shown in FIG. 3 and 4, the positions 14 can be physically adapted or modified for particular clamps. Even if the elongated body 2 is smooth in this region (using, for example, a gripping-type clamp), it would still be desirable if the acceptable distances x and/or y are visibly marked to assist the surgeon in proper clamp placement. For example, the preferred distance from about 5 to about 20 mm distal to electric pole 40 could be color coded; likewise, the preferred distance from about 5 to about 15 mm proximal to electric pole 41. Preferably, the colors (or other visible markers) would be different on the proximal and distal clamping positions so as to be easily distinguished by the surgeon. Alternatively, the relevant distances or ranges could be printed directly on the elongated body for both the proximal and distal clamping positions.

FIGS. 5 illustrates the electrocatheter of this invention properly located in tissue to be treated. Using the penetration mechanism (reference number 6 in FIGS. 1–3), the implant is inserted through the tissue wall 300 (e.g., stomach wall) into the underlying tissue or muscle 302 and then back through the tissue wall 300. The penetration mechanism forms a penetration tunnel having a proximal terminus 310 and a distal terminus 312. The implant is then pulled through the penetration tunnel until clamp 300B contacts, and is held by, the tissue at the proximal terminus 310. The distance from the clamp 200B to electric pole 41 is greater than about 5 mm and preferably is about 5 mm to about 15 mm. As shown in FIG. 5, the elongated body 2 exits at the distal terminus 312 of penetration tunnel. Once the implant is properly positioned within the penetration tunnel, clamp 200A is affixed to lock the implant in place. The distance from the clamp 200A to electric pole 40 is greater than about 5 mm and preferably is about 5 to about 20 mm. FIG. 5 illustrates the proper positioning of the electric leads 40 and 41 within the penetration tunnel to insure good electrical contact with the tissue to be treated. The distance between the electric poles can be varied as needed. The length of the penetration tunnel should be approximately equal to, or less than, the sum of the distance from the clamp 200B to electric pole 41, the distance between the electric poles 40 and 41, and the distance from the clamp 200A to electric pole 40 to insure proper location of the electric poles 40 and 41 within the penetration tunnel. Generally it is preferred that the length of the penetration tunnel is less than this sum; more preferably, the length of the penetration tunnel is at least about 1 to about 2 mm less than this sum. An overall distance from clamp 200A to clamp 200B equal to or less than the length of the penetration tunnel significantly reduces the risk that one of the electric poles can migrate or work its way out of the penetration tunnel even when the tissue is undergoing significant movement. Markings on the stylet 8 (e.g., illustrating the distance between the two electrodes) can used to guide the surgeon in forming the penetration tunnel of the proper length.

FIG. 6 illustrates a similar electrocatheter within a penetration tunnel except that the clamp 200B has been replaced with tines 15. In many instances, it will be preferred to have proximal immobilizing mechanisms which are integral with the elongated body and distal immobilizing mechanisms which can be placed as needed by the surgeon during the implantation procedure. In such a case, the implant is pulled through the penetration tunnel until the fixed tines 15 engage the proximal terminus; the single clamp 200A would then be placed at the distal terminus of the penetration tunnel.

Several suitable clamps are illustrated in FIG. 7. The clamp 200 in FIG. 7A is specifically designed to fit the clamping position 14A in FIG. 3 or positions 14A, 14B, or 14C in FIG. 4. More specifically, the upper ring 202 and lower ring 204 are designed to fit within position 14A. The upper ring 202 and lower ring 204 are attached via hinge 206. When closed around the elongated body, the clamp is held in the closed position using locking mechanisms 212 and 214. Any suitable locking mechanism known in the art can be used. The wings 208 and 210 are to engage the tissue at the distal or proximal terminus of the penetration tunnel to lock the implant in proper position within the penetration tunnel. The wings 208 and 210 may be integral with, or simply attached to, their respective upper and lower rings 202 and 204. Other shaped clamps and corresponding clamping positions on the elongated body can be used. One such configuration is illustrated in FIG. 8 wherein the upper and lower clamping rings 202 and 204 have mating surfaces 222 which correspond to, and mate with, surfaces 220 at position 14A on the elongated body 2.

Another clamp 200 with serrated teeth 216 is shown in FIG. 7B. This clamp has an upper jaw 208 and a lower jaw 204, connected with hinge 206. Again a locking mechanism 212 and 214 is provided so that the surgeon can lock the clamp onto the elongated body at the appropriate position. Of course, other known clamps known in the medical field can be used.

Generally, the clamps are formed from bio-compatible materials such as, for example, silicone, titanium, stainless steel, and the like. The clamps should, of course, not have sharp or jagged edges or surfaces which might damage the tissue. Such clamps can, if desired, be manufactured using a suitable metal or hard plastic and then coated with a softer, bio-compatible material (e.g., silicone) to further reduce the likelihood of tissue injury. When removing the implant, the distal clamp can be removed (or cut off) from the elongated body and the remaining implant structure "backed out" of the penetration tunnel.

The implant devices of the present invention are especially adapted to provide electrical stimulation to the stomach for treating obesity and/or syndromes related to motor disorders of the stomach as described in U.S. Pat. No. 5,423,872 (issued Jun. 13, 1995). The stomach generally has three layers of smooth muscle—oblique, circular, and longitudinal muscle layers. The myenteric plexus (or Auerbach plexus) is generally located intermediate to the circular and longitudinal muscle layers while the submucous plexus (or Meissner plexus) is generally located intermediate to the oblique and circular muscle layers. It is generally preferred that the present implant device, when used to stimulate the stomach, is located such that Auerbach plexus, and more preferably both the Auerbach plexus and the Meissner plexus, are stimulated. Thus, in one embodiment, it is preferred that the penetration tunnel is formed within the stomach wall so as to allow for stimulation of the Auerbach plexus and the Meissner plexus. By situating the penetration tunnel through or adjacent to these nerve complexes (and thus the electrode leads once the implant has been properly positioned within the penetration tunnel), more effective direct stimulation of the nerves (as well as stimulation of the smooth muscle) can be effected. Alternatively, the Auerbach plexus and the Meissner plexus can be stimulated by placing the implant of this invention or other electrostimulation implants adjacent to the Auerbach plexus and the Meissner plexus so as to provide electrostimulation of the Auerbach plexus and the Meissner plexus; in such cases, a penetration tunnel would, of course, not be required.

It has been proven in practice that the implant device according to the invention is particularly useful as stated above. The invention so described may be subject to numerous modifications and variations, all of which fall within the scope of the inventive concept; furthermore, all the details may be replaced by technically equivalent elements. In practice, the materials used, as well as the dimensions, may be varied according to need and the state of the art. Although this implant device has been mainly described relative to its use in the gastrointestinal tube, it is primarily intended to be used in the endo-abdominal cavity including all viscera therein; such viscera include, but are limited to, tissues associated with the stomach, large and small intestines, gall bladder, urinary tract, bladder, muscles, and the like. Moreover, although this implant device has been described in the context of use within the endo-abdominal cavity, it can, of course, be used in other portions of the body with appropriate modifications.

What is claimed is:

1. An implant device for electrostimulation or electrical monitoring of tissue to be treated within a body cavity, said implant device comprising
   (1) an elongated body having a distal end and a proximal end,
   (2) a penetration mechanism at the distal end to penetrate the tissue to be treated,
   (3) a quick release connecting mechanism adjacent to the penetration mechanism,
   (4) a first immobilizing mechanism and a second immobilizing mechanism adjacent and proximal to the quick release connecting mechanism to secure the implant device to the tissue to be treated wherein the first and second immobilizing mechanisms are spaced apart along the elongated body a distance sufficient to span the tissue such that the first immobilizing mechanism is located between the quick release connecting mechanism and the second immobilizing mechanism,
   (5) a first and second electric poles located between the first and second immobilizing mechanisms, such that the first electric pole is adjacent to the first immobilizing mechanism and the second electric pole is adjacent to the second immobilizing mechanism, and
   (6) an electrical connection terminal at the proximal end for connection to a power source;
   wherein the first and second electric poles are electrically connected to the electrical connection terminal; wherein the quick release connecting mechanism is effective to separate the penetration device from the elongated body once the implant device is properly positioned in the body cavity; and wherein the first immobilizing mechanism is located at a distance of about 5 mm or greater from the first electric pole and the second immobilizing mechanism is located at a distance of about 5 mm or greater from the second electric pole.

2. The implant device as defined in claim 1, the distance from the first immobilizing mechanism to the first electric pole is about 5 to about 20 mm and the distance from the second immobilizing mechanism to the second electric pole is about 5 to 15 mm.

3. The implant device as defined in claim 2, wherein the first and second immobilizing mechanisms are sets of flexible and angled tines, such that the tines of the first immobilizing mechanism form an acute angle relative to the first electric pole and the tines of the second immobilizing mechanism form an acute angle relative to the second electric pole.

4. The implant device as defined in claim 2, wherein the first immobilizing mechanism is a clamp to be attached to the elongated body once the implant device is properly positioned in the endo-abdominal cavity and the second immobilizing mechanism is a set of flexible and angled tines, such that the tines form an acute angle relative to the second electric pole.

5. The implant device as defined in claim 4, wherein the elongated body has at least one position adapted to accept the clamp.

6. The implant device as defined in claim 2, wherein the first immobilizing mechanism is a first clamp to be attached to the elongated body once the implant device is properly positioned in the endo-abdominal cavity and the second immobilizing mechanism is a second clamp to be attached to the elongated body either before or after the implant device is properly positioned in the endo-abdominal cavity.

7. The implant device as defined in claim 4, wherein the elongated body has at least one position adapted to accept the first clamp.

8. An implant device for electrostimulation or electrical monitoring of tissue to be treated within the endo-abdominal cavity, said implant device comprising
   (1) an elongated body having a distal end and a proximal end,
   (2) a penetration mechanism at the distal end to penetrate the tissue to be treated and to form a penetration tunnel though the tissue, wherein the penetration tunnel has a distal terminus and a proximal terminus and a length as measured from the distal terminus to the proximal terminus through the penetration tunnel,
   (3) a quick release connecting mechanism adjacent to the penetration mechanism,
   (4) a first immobilizing mechanism and a second immobilizing mechanism, wherein the second immobilizing mechanism is attached to, and integral, with the elongated body and is proximal to the quick release connecting mechanism such that second immobilizing unit will engage the proximal terminus of the penetration tunnel and wherein the first immobilizing mechanism is adapted to be affixed to the elongated body as its exits the distal terminus of the penetration tunnel to secure the implant device to the tissue to be treated,
   (5) a first and second electric poles located between the first and second immobilizing mechanisms, such that the first electric pole is adjacent to the first immobilizing mechanism and the second electric pole is adjacent to the second immobilizing mechanism and wherein the first and second electric poles are in good electrical contact with the tissue forming the penetration tunnel, and
   (6) an electrical connection terminal at the proximal end for connection to a power source;
   wherein the first and second electric poles are electrically connected to the electrical connection terminal; wherein the quick release connecting mechanism is effective to separate the penetration device from the elongated body once the implant device is properly positioned in the endo-abdominal cavity; wherein the first immobilizing mechanism is located at a distance of about 5 mm or greater from the first electric pole and the second immobilizing mechanism is located at a distance of about 5 mm or greater from the second electric pole, and wherein the first and second immobilizing mechanism are spaced apart a distance approximately equal to, or less than, the length of the penetration tunnel.

9. The implant device as defined in claim 8, wherein the distance from the first immobilizing unit to the first electric pole is about 5 to about 20 mm and the distance from the second immobilizing mechanism to the second electric pole is about 5 to about 15 mm.

10. The implant device as defined in claim 8, wherein the second immobilizing mechanism is a set of flexible and angled tines, such that the tines form an acute angle relative to the second electric pole, and wherein the elongated body has at least one position adapted to accept the first immobilizing mechanism.

11. The implant device as defined in claim 9, wherein the second immobilizing mechanism is a set of flexible and angled tines, such that the tines form an acute angle relative to the second electric pole, and wherein the elongated body has at least one position adapted to accept the first immobilizing mechanism.

12. The implant device as defined in claim 8, wherein the penetration mechanism has spaced-apart markings to visually assist and guide a surgeon as the penetration tunnel is formed.

13. An implant device for electrostimulation or electrical monitoring of tissue to be treated within the endo-abdominal cavity, said implant device comprising (1) an elongated body having a distal end and a proximal end, (2) a penetration mechanism at the distal end to penetrate the tissue to be treated and to form a penetration tunnel though the tissue, wherein the penetration tunnel has a distal terminus and a proximal terminus and a length as measured through the penetration tunnel from the proximal terminus to the distal terminus, (3) a quick release connecting mechanism adjacent to the penetration mechanism, (4) a first immobilizing mechanism which can be attached to the elongated body to secure it in place within the penetration tunnel once the elongated body is properly positioned relative to the tissue to be treated and a second immobilizing mechanism which can be attached to the elongated body to secure it in place within the penetration tunnel either before or after the elongated body is properly positioned relative to the tissue to be treated, wherein the first immobilizing mechanism is adapted to be attached to the elongated body at the distal terminus of the penetration tunnel and the second immobilizing mechanism is adapted to be attached to the elongated body at the proximal terminus of the penetration tunnel, (5) a first electric pole and a second electric pole spaced apart along the elongated body to be contained within the penetration tunnel and to be in good electrical contact with the tissue forming the penetration tunnel, and (6) an electrical connection terminal at the proximal end for connection to a power source;

wherein the first and second electric poles are electrically connected to the electrical connection terminal; wherein the quick release connecting mechanism is effective to separate the penetration device from the elongated body once the implant device is properly positioned in the endo-abdominal cavity; wherein, when the first and second electric poles are properly situated within the penetration tunnel, the first immobilizing mechanism is located at a distance of about 5 mm or greater from the first electric pole and the second immobilizing mechanism is located at a distance of about 5 mm or greater from the second electric pole, and wherein the first and second immobilizing mechanism are spaced apart a distance approximately equal to, or less than, the length of the penetration tunnel.

14. The implant device as defined in claim 13, wherein the distance from the first immobilizing mechanism to the first electric pole is about 5 to about 20 mm and the distance from the second immobilizing mechanism to the second electric pole is about 5 to about 15 mm.

15. The implant device as defined in claim 14, wherein the first immobilizing mechanism is a first clamp.

16. The implant device as defined in claim 15, wherein the second immobilizing mechanism is a second clamp.

17. The implant device as defined in claim 15, wherein the elongated body has at least one clamping position adapted to accept the first clamp.

18. The implant device as defined in claim 17, wherein the elongated body has at least one clamping position adapted to accept the second clamp.

19. A laparoscopic surgical method for attaching an implant device to tissue to be treated, said method comprising (a) inserting an implant device though a trocar into a body cavity containing the tissue to be treated, wherein the implant device has a penetration mechanism and a first and second electric poles, (b) forming a penetration tunnel within the tissue to be treated using the penetration mechanism, wherein the penetration tunnel has a distal terminus and a proximal terminus and a length as measured through the penetration tunnel from the proximal terminus to the distal terminus, (c) positioning the first and second electric poles within the penetration tunnel to provide good electrical contact with the tissue to be treated, and (d) immobilizing the implant device within the penetration tunnel so as to maintain good electrical contact between the first electric pole and the tissue to be treated and between the second electric pole and the tissue to be treated during a treatment regime;

wherein the implant device comprises (1) an elongated body having a distal end and a proximal end, (2) penetration mechanism which is located at the distal end to penetrate and to form the penetration tunnel in the tissue to be treated, (3) a quick release connecting mechanism adjacent to the penetration mechanism, (4) a first immobilizing mechanism and a second immobilizing mechanism adjacent and proximal to the quick release connecting mechanism to immobilize the implant device to the tissue to be treated wherein the first and second immobilizing mechanisms are spaced apart along the elongated body a distance sufficient to span the tissue such that the first immobilizing mechanism is located between the quick release connecting mechanism and the second immobilizing mechanism, (5) first and second electric poles which are located between the first and second immobilizing mechanisms, such that the first electric pole is adjacent to the first immobilizing mechanism and the second electric pole is adjacent to the second immobilizing mechanism, and (6) an electrical connection terminal at the proximal end for connection to a power source;

wherein the first and second electric poles are electrically connected to the electrical connection terminal; wherein the quick release connecting mechanism is effective to separate the penetration device from the elongated body once the first and second electric poles are properly positioned within the penetration tunnel; and wherein, when the first and second electric poles are properly situated within the penetration tunnel, the first immobilizing mechanism is located at a distance of about 5 mm or greater from the first electric pole and the second immobilizing mechanism is located at a distance of about 5 mm or greater from the second electric pole, and wherein the first and second immobilizing mechanism are spaced apart a distance approximately equal to, or less than, the length of the penetration tunnel.

20. The method as defined in claim 19, wherein distance from the first immobilizing mechanism to the first electric pole is about 5 to about 20 mm from the first electric pole and the distance from the second immobilizing mechanism to the second electric pole is about 5 mm to about 15 mm from the second electric pole.

21. The method as defined in claim 20, wherein the first and second immobilizing mechanisms are sets of flexible and angled tines, such that the tines of the first immobilizing mechanism form an acute angle relative to the first electric pole and the tines of the second immobilizing mechanism form an acute angle relative to the second electric pole.

22. The method as defined in claim 20, wherein the first immobilizing mechanism is a clamp to be attached to the elongated body once the implant device is properly positioned in the penetration tunnel and the second immobilizing mechanism is a set of flexible and angled tines, such that the tines form an acute angle relative to the second electric pole.

23. The method as defined in claim 22, wherein the elongated body has at least one position adapted to accept the clamp.

24. The method as defined in claim 20, wherein the first immobilizing mechanism is a first clamp to be attached to the elongated body once the implant device is properly positioned in the penetration tunnel and the second immobilizing mechanism is a second clamp to be attached to the elongated body either before or after the implant device is properly positioned in the penetration tunnel.

25. The method as defined in claim 24, wherein the elongated body has at least one position adapted to accept the first clamp.

26. A method for electrostimulation of gastrointestinal tissue, said method comprising (a) inserting an implant device though a trocar into the endo-adominal cavity, wherein the implant device has a first and second electric poles and an electrical connection terminal for connection to an electrical pulse generator, (b) positioning the first and second electric poles within an area of the gastrointestinal track to provide good electrical stimulation with the Auerbach plexus and the Meissner plexus, (c) immobilizing the implant device so as to maintain good electrical stimulation of the Auerbach plexus and the Meissner plexus during a treatment regime, (d) attaching the electrical pulse generator to the electrical connection terminal of the implant device, and (e) delivering electrical impulses to the implant device and thereby electrically stimulating the Auerbach plexus and the Meissner plexus.

27. The method as defined in claim 26, wherein the gastrointestinal tissue to be treated is stomach tissue.

* * * * *

UNITED STATES PATENT AND TRADEMARK OFFICE
CERTIFICATE OF CORRECTION

PATENT NO.    : 6,381,495 B1
DATED         : April 30, 2002
INVENTOR(S)   : David A. Jenkins It is certified that error appears in the above-identified patent and that said Letters Patent is hereby corrected as shown below:

Title page,
Item [30], Foreign Application Priority Data, change "May 29, 1997" to -- May 28, 1997 --.

Column 20,
Line 21, change "endo-adominal" to -- endo-abdominal --.

Signed and Sealed this

Eighth Day of October, 2002

Attest:

JAMES E. ROGAN
Attesting Officer    Director of the United States Patent and Trademark Office